United States Patent
Nierich

(10) Patent No.: US 7,780,599 B2
(45) Date of Patent: Aug. 24, 2010

(54) TRANSMISSION DEVICE FOR ULTRASONIC IMAGING SYSTEM

(75) Inventor: Arno Nierich, Hattem (NL)

(73) Assignee: Cordatec NV, Zoersel (BE)

( * ) Notice: Subject to any disclaimer, the term of this patent is extended or adjusted under 35 U.S.C. 154(b) by 648 days.

(21) Appl. No.: 11/454,470

(22) Filed: Jun. 16, 2006

(65) Prior Publication Data

US 2007/0038109 A1    Feb. 15, 2007

Related U.S. Application Data

(63) Continuation-in-part of application No. 10/221,250, filed as application No. PCT/EP00/02212 on Mar. 10, 2000, now abandoned.

(30) Foreign Application Priority Data

Mar. 10, 1999    (EP)    .................................. 99200703

(51) Int. Cl.
*A61B 8/12*    (2006.01)
(52) U.S. Cl. ........................ 600/443; 600/462
(58) Field of Classification Search ................. 600/437, 600/443, 459, 462, 463, 466, 470
See application file for complete search history.

(56) References Cited

U.S. PATENT DOCUMENTS

| 3,766,927 | A | * | 10/1973 | Jackson | ................. | 128/207.15 |
|---|---|---|---|---|---|---|
| 3,779,234 | A | | 12/1973 | Eggleton et al. | | |
| 3,800,788 | A | * | 4/1974 | White | .......................... | 606/86 |
| 3,810,474 | A | * | 5/1974 | Cross | ..................... | 128/207.15 |
| 4,349,033 | A | | 9/1982 | Eden | | |
| 4,391,282 | A | * | 7/1983 | Ando et al. | .................. | 600/463 |
| 4,466,443 | A | | 8/1984 | Utsugi | | |
| 4,886,059 | A | * | 12/1989 | Weber | ......................... | 600/471 |
| 4,906,244 | A | * | 3/1990 | Pinchuk et al. | .............. | 606/194 |
| 4,979,505 | A | * | 12/1990 | Cox | ....................... | 128/207.15 |
| 5,105,819 | A | | 4/1992 | Wollschläger et al. | | |
| 5,190,046 | A | | 3/1993 | Shturman | | |
| 5,331,947 | A | * | 7/1994 | Shturman | .................... | 600/115 |
| 5,785,051 | A | * | 7/1998 | Lipscher et al. | ......... | 128/207.15 |
| 6,689,062 | B1 | * | 2/2004 | Mesallum | .................... | 600/439 |

FOREIGN PATENT DOCUMENTS

JP    06285068 A  *  10/1994

* cited by examiner

*Primary Examiner*—Eric F Winakur
(74) *Attorney, Agent, or Firm*—The Webb Law Firm

(57) ABSTRACT

The invention relates to an ultrasonic imaging system having an ultrasound intra-esophageal endoscope device for scanning a patient's organs, for use in particular with transesophageal echocardiography, and an intratracheal transmission device defining a transmission path for sound waves originating from the endoscope device. A transmission device is specially adapted for use with an endoscope device in an ultrasonic imaging system having a flexible balloon member connected to a supply line for a sound wave transmission fluid medium.

18 Claims, 3 Drawing Sheets

TRANSMISSION DEVICE FOR ULTRASONIC IMAGING SYSTEM

CROSS REFERENCE TO RELATED APPLICATIONS

This application is a continuation-in-part application of U.S. application Ser. No. 10/221,250, filed Sep. 10, 2002, which claims the benefit of priority to PCT Application No. PCT/EP00/02212, filed Mar. 10, 2000 and European Application No. 99200703.9, filed Mar. 10, 1999, which are incorporated herein by reference in their entirety.

BACKGROUND OF THE INVENTION

1. Field of the Invention

The invention relates to an ultrasonic imaging system comprising an ultrasound endoscope device for scanning a patient's organs, in particular for use in transesophageal echocardiography.

2. Description of the Prior Art

Such a device specially adapted for transesophageal echographic scanning is for example disclosed in U.S. Pat. No. 5,105,819.

Transesophageal echocardiography (TEE) has become a widely used imaging technique for evaluating cardiac structure, function, and valvular anatomy. Transesophageal echocardiography has also provided a new perspective on the thoracic aorta, and there is growing evidence that the technique contributes valuable and sometimes unique information about aortic structure and pathology.

Two-dimensional (2D) transesophageal echocardiography (TEE) and 2D intravascular ultrasound (IVUS) imaging face their greatest limitation in visualizing aortic disease in patients. Recently introduced multi-plane transesophageal probes have improved visualization of the proximal and transverse aorta. Three-dimensional (3D) image reconstruction, TEE and IVUS can even improve further visualization but still provide only limited spatial appreciation in aortic disease because 3D imaging of the thoracic aorta requires a broader spatial visualization of the mediastinum than provided by both techniques. Another approach called 3D lighthouse transesophageal echocardiography (LTEE) uses a thin intravascular ultrasound catheter, which provides a full circumferential (360 degree) image, but is invasive and cannot be used during cardiac surgery with cardio-pulmonary bypass. Also these three methods (3D, IVUS, and LTEE) need special ultrasound equipment, which is not standard available.

The available evidence strongly supports the use of TEE in aortic dissection and atherosclerosis and suggests potential utility in additional diseases of the aorta such as aneurysm, ulceration, trauma, and congenital or inherited malformations.

The features of ultrasonic imaging systems cause main problems in visualization of certain organs in particular of the upper mediastinum, including the ascending aorta.

To understand these problems, it is important to know the physical limitations of ultrasound. Ultrasound consists of sound waves. The signal is determined by:
1. Frequency, f is determined by the generator.
2. Velocity, v is determined by the medium.
3. Wavelength, λ is the distance between two cycles of sound waves.

Absorption of sound waves is dependent of the medium. This is reflected as the half power distance: The distance in which half of the ultrasound energy will be absorbed. For water this is 380 cm, bone 10, 2 cm and for air 0, 06 cm. This means that nor bone nor air will not let through ultrasound waves in practice.

Consequently, the prior art does not achieve good imaging results, if air or bone are between the ultrasound source and the area which are to be investigated.

SUMMARY OF THE INVENTION

In providing a solution to this problem the invention is directed towards an ultrasonic imaging system as specified in claim 1.

Providing a separate transmission device at a distance of the ultrasound endoscope thus providing a transmission path suitable for sound waves originating from the endoscope device. Visualization will be surprisingly enhanced using a device according to the invention.

In a preferred embodiment of the invention the transmission device comprises a flexible housing for receiving a sound wave transmission fluid medium. As an example of such a sound wave transmission fluid water or a salt solution in minor concentrations is preferred.

A further preferred embodiment provides a transmission device which is formed by a distensible balloon member connected to a supply line to permit fluid entry in said balloon member.

According to another aspect of the invention a transmission device is provided which is specially adapted for use in association with an endoscope device in an ultrasonic imaging system comprising a flexible balloon member connected to a supply line for a sound wave transmission fluid medium.

Further, the present invention is also directed towards the use of an ultrasonic imaging system and to a method for ultrasonic scanning a patient's organs.

Embodiments of the present invention are described below by way of example only. In a preferred embodiment of the invention the ultrasonic imaging system according to the invention is directed to the use in transesophageal echocardiography. It will become apparent that not only a specialized doctor could use the ultrasonic imaging system according to the invention, but also a skilled technician.

Echocardiography was first used solely by cardiologist by the transthoracic approach in the awake patient. Visualization is sometimes difficult by the bone (sternum) and air (lung) structures between the echo probe and the heart. With the development of the transesophageal echocardiography, this problem is largely avoided. The disadvantage is more patient discomfort in the awake situation. Now only small parts of the cardiac structures and surrounding tissues are still difficult or impossible to image by this way. Since TEE is an excellent way of monitoring cardiac function, other specialties, like cardiac anaesthesiologists started to use this technique. It is even so that nowadays cardiac anaesthesiologists are trained to use TEE in the perioperative period of cardiac surgery without the interference of the cardiologist. The advantage is that during surgery the patient is asleep, so discomfort is not a problem. During cardiac surgery, a patient is paralysed, intubated in the trachea and mechanically ventilated. If the patient is on cardiopulmonary bypass, the ventilation is stopped since there is no blood flowing through the lungs and oxygenation is provided by the heart lung machine. Placing the echoprobe into the trachea is technically possible but limits the echo investigation to the upper part of the mediastinum and does not evaluate the heart like with TEE, which is a standard technique perioperative.

Visualization by external transthoracic echocardiography is limited by the bone structures between the echoprobe and the ascending aorta. During heart surgery with a split sternum this problem is overcome by epi-aortic scanning. However, only a part of the aorta is visualized by the surgeon during surgery and an additional echoprobe besides the TEE probe is needed. Visualization by internal transesophageal echocardiography of the ascending aorta is limited by an air structure, i.e. the trachea and main left and right bronchii. By the anatomical location of the Aorta ascendens and the upper part of the main vascular side branches, it is difficult to view this area by TEE because the view is obstructed by the trachea. The trachea is located between the esophagus and the vascular tree, so all echoes are reflected by the trachea, which is filled with air.

A possible solution is to fill the trachea with a medium not containing air, but with a medium which will absorb ultrasound signal less, like water. In the normal patient, this is not possible, but in the anesthetized patient or a patient on extracorporeal bypass, it is possible to stop ventilation for a certain period of time. Oxygenation can be maintained by preoxygenation to a safe period of 4 minutes. If the patient is on extracorporeal circulation, this time-period is at least one hour. Filling the lungs completely with water is not possible, but introducing a transmission device into the trachea, like a balloon which can be filled and emptied from outside the patient, would allow ultrasound to travel through the tracheal structure without absorption. This would allow visualization of structures in front of the trachea.

After the patient is intubated there is an easy access route to the distal trachea. The average diameter is 1.7 cm, the average distance to occlude is maximum 10 cm. An inflatable balloon connected to a small extension tube with distally multiple holes allows easy insertion in the trachea. If the material is easily distensible, it will line up against the tracheal wall and might even fill up the right and/or left main bronchi. The trachea wall is not fully round and is vulnerable, so the material of the balloon must be flexible and there must be a possibility to monitor the pressure inside the device to prevent barotrauma of the trachea by overdistension of the balloon. This can be accomplished by a safety valve, a pressure monitor or a (external) pilot balloon at the end of the flexible extension tube. This extension line must be thin with a diameter of approximately 2-3 mm, stiff to allow easy insertion by the tracheal tube without kinking.

By the side holes in the tube water can be inserted in the balloon, so the ballon will distend and occlude the trachea. Air in the trachea will not obstruct TEE view and an view of the upper mediastinum will be obtained. After the TEE examination the water can be aspirated by suction on the tube and if empty, it is easily removed from the ventilation tube or directly out of the trachea.

Examples of clinical applications of the transmission device of the invention.

1. Aortic atherosclerosis.
In cardiac surgery, it is important to obtain information regarding the ascending aorta. Atherosclerosis of the cannulation site is an important source of emboli. It is just this area which is difficult to scan until now. By introducing the transmission device after induction of anesthesia with tracheal intubation, a first screening of this area can be performed, also in non-cardiac situations. Surgical strategy can be altered if atherosclerosis is a fact, e.g. femoral artery cannulation, beating heart surgery without CPB, aortic arch replacement, et al.
2. Aortic dissection.
Aortic dissection and its diagnosis are major clinical problems. Dissections can start at all sides of the aortic root. However the clinical treatment is dependent on the location and the extension of the rupture of the aortic wall. A rupture in the ascending or transverse aorta is treated by surgery, a dissection in the descending aorta by medication treatment. Also the extension of a dissection in the main branches of the aorta can be evaluated. This way of evaluation would allow a fast diagnosis, in contrast to Computer tomography or angiography, thus reducing time loss before surgery.
3. Carotid disease.
In patients at risk for having atherosclerosis, an evaluation can be made during all forms of anesthesia, in order to evaluate carotid disease. Flow measurements can be made by doppler ultrasound.
4. Cardiac output monitoring.
The aortic arch will be viewed by crossectional view. To use the echodoppler feature of ultrasound, the moving object must be viewed within an angle of 30 degrees. By measuring the anatomical diameter and by measuring the blood flow, cardiac output can be calculated. Without this device this can be performed by viewing the aortic valve by looking at this valve from the deep transgastric direction. This view is sometimes difficult to obtain, like by example during beating heart coronary artery bypass grafting.
5. Monitoring of flow and intravascular lines during CPB.
The aortic CPB line will be inserted in the ascending aorta. Appropriate flow can be visualized.
During a Heartport procedure an intra-aortic balloon must be placed just above the aortic valve but below the truncus brachiocephalicus. The flow of all sections can be easily monitored now.
Intra aortic balloon counterpulsation is a device which is used as an assist device in cardiac failure. Flow patterns can be measured to optimize timing of balloon inflation and deflation in order to optimize the effectivity of this device.
6. Monitoring of embolism during surgery.
7. Pulmonary embolism.
The visualization of the left and right pulmonary artery is partially obstructed by the main bronchii. The blocker might allow this view.

DESCRIPTION OF THE PREFERRED EMBODIMENTS

Figure 1:
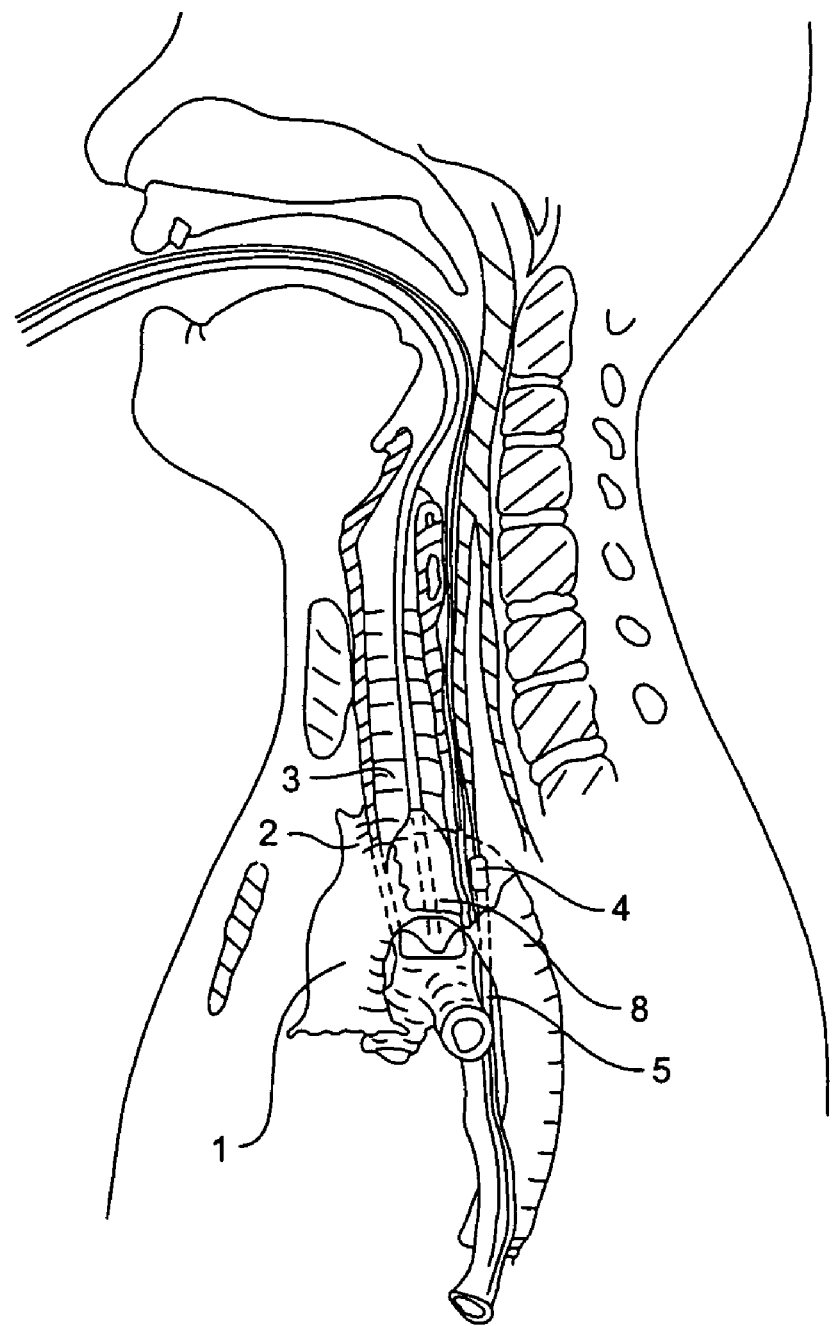
FIG. 1 is a schematic view of the anatomical location of the aorta, the trachea and the esophagus in relation to the system according to the invention.

As explained in the description visualization of the aorta ascendens 1 and the upper part of the main vascular side branches 2 is difficult to view because an obstruction of the trachea 3 disturbs the ultrasound waves originating from an echoprobe 4 in the esophagus 5. When a patient is intubated with a transmission device according to the invention, which normally consists of a distensible balloon connected to a supply line for a sound wave transmission fluid medium, a suitable sound wave path is formed for the sound waves originating from an ultrasound endoscope positioned in the esophagus 5. An optimal visualization of these parts of the aorta is thus obtained by a combined use of an endoscope device and a transmission device forming an ultrasonic imaging system according to the invention.

Figure 2:
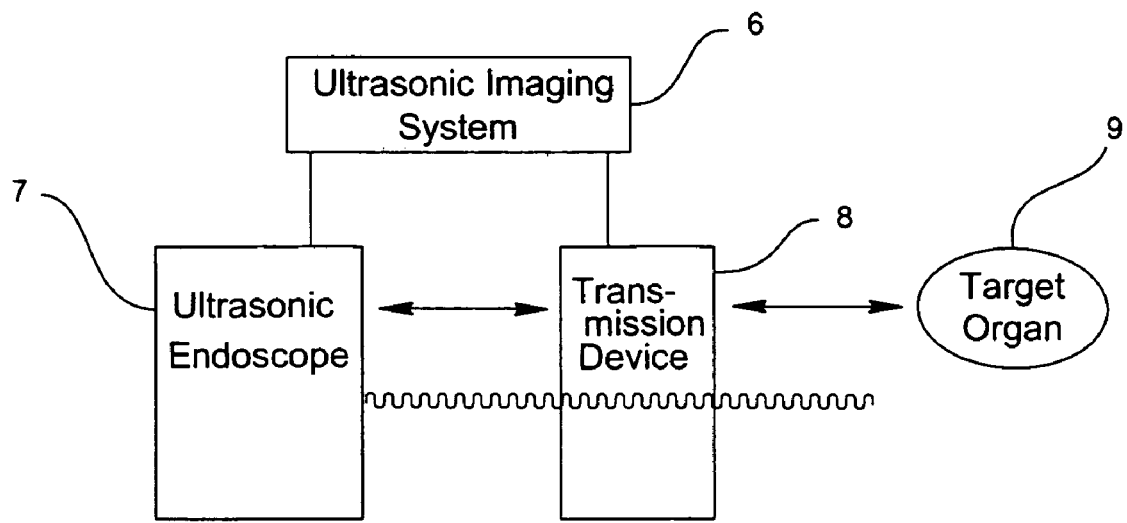
FIG. 2 is a schematic view of an ultrasonic imaging system according to the invention.
Figure 3:
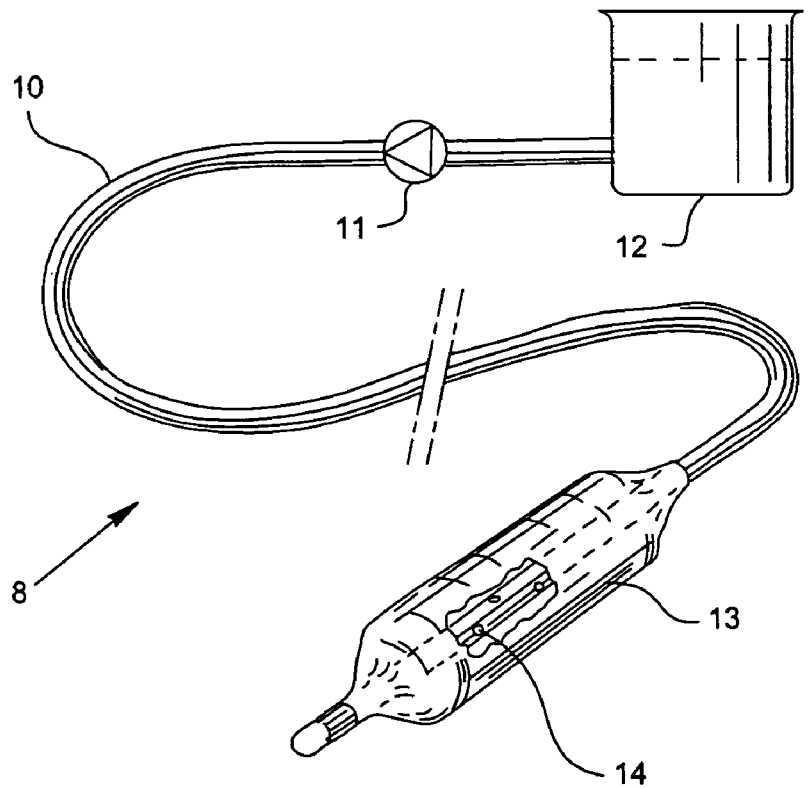
FIG. 3 is a perspective view of a preferred embodiment of a transmission device according to the invention.

FIG. 2 shows very schematically an ultrasonic imaging system 6 comprising an ultrasound endoscope 7 and a separate transmission device 8. When viewed with a target organ 9 ultrasound waves originating from the ultrasound endoscope 7 will have a suitable transmission path and where no such path is provided, for example in cavities with air, a separate transmission device 8 is introduced in order to replace the air with a sound wave transmission fluid medium, such as water or a salt solution.

A separate transmission device 8 generally consists of a flexible, distensible balloon member 13 which is connected to a supply line 10 which supply line 10 is at its distal end provided with pump and pressure control means 11 and is further connected to a container 12 which is provided with the sound wave transmission fluid. The supply line 10 is provided with perforations 14 at the proximal end in the volume of the flexible balloon member 13. These perforations 14 permit filling and emptying the balloon 13 over the entire volume and no air inclusion will occur.

Figure 4A:
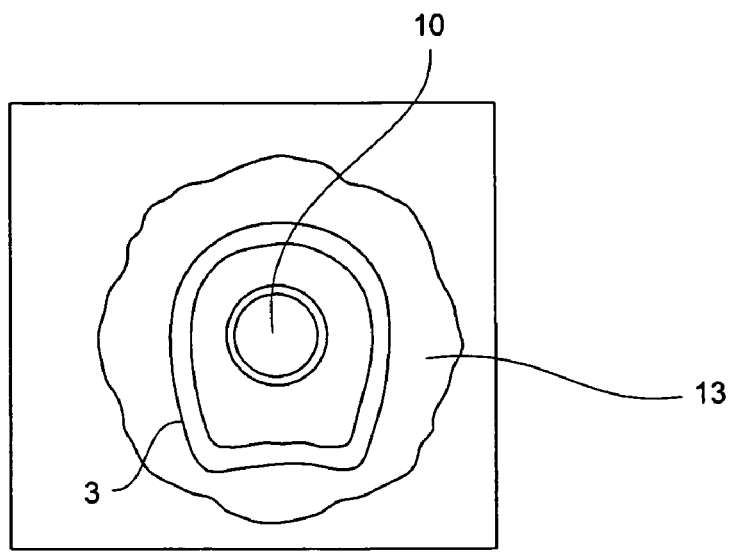
FIGS. 4A-4D are schematic cross-sectional views illustrating the balloon member of the transmission device and the trachea at various stages of filling the balloon member.

The flexible, distensible balloon 13 may be "oversized" in relation to the trachea 3, in the sense that its circumferential dimension when filled with fluid is greater than the inner circumference of the trachea 3, as illustrated in FIG. 4A. In this way the balloon 13 will conform closely to the inside of the trachea, while excess material of the balloon 13 will form inwardly directed folds 15, thus effectively sealing the trachea 3.

Figure 4B:
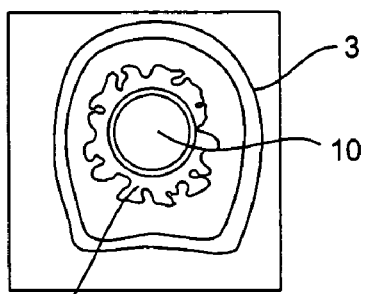
Figure 4C:
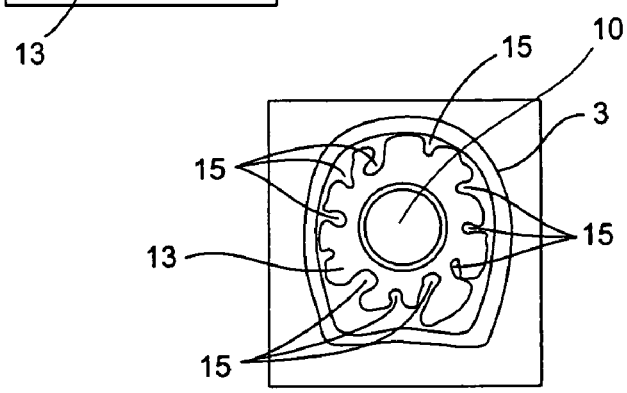
Figure 4D:
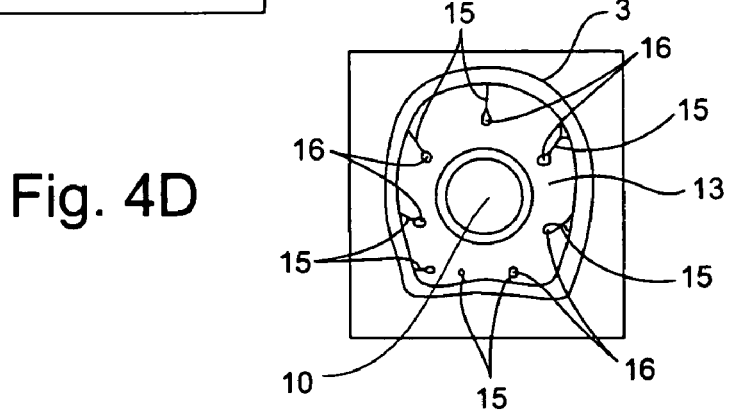

In order to obtain an optimum seal, the wall thickness of the balloon 13 should be reduced as much as possible. In that manner the inner ends 16 of the folds 15, which will assume something of a droplet shape, are kept as small as possible. When the balloon 13 is made from polyurethane or a polyurethane based synthetic material, wall thicknesses in the order of 2 to 25 microns, and preferably 5 to 10 microns may be obtained. Such small thicknesses also allow the balloon 13 to be unfolded against the inside of the trachea 3 at very low fluid supply pressures, thus minimizing the risk of causing barotrauma to the trachea 3. In practice, the pressure control means 11 may be set to a value of 30 mbar or less. The various stages of unfolding the balloon 13 are illustrated in FIGS. 4B, 4C and 4D, which clearly show the close conformity of the balloon 13 to the inside of the trachea 3 and the formation of the folds 15.

The invention claimed is:

1. An ultrasonic imaging system, comprising an ultrasound endoscope device for scanning a patient's organs and a transmission device defining a transmission path for sound waves originating from the endoscope device, the transmission device being formed by a distensible balloon member connected to a supply line to permit fluid entry to the balloon member, wherein the balloon member and supply line are shaped and dimensioned so as to be inserted into the patient's trachea, thus forming an intra-tracheal transmission device, wherein the endoscope device is arranged spatially separated from the balloon member and is shaped and dimensioned so as to be inserted into the patient's esophagus, thus forming an intra-esophageal endoscope device, the balloon member adapted to occlude the trachea when inserted in the trachea and filled with a sound transmission fluid, so as to form a sound wave path for waves originating from the endoscope when positioned in the esophagus, which allows the ultrasonic imaging system to be used in transesophageal echocardiography to view structures through the trachea.

2. The ultrasonic imaging system according to claim 1, wherein the supply line has a stiffness that is sufficient to avoid kinking upon insertion of the transmission device into the patient's trachea.

3. The ultrasonic imaging system according to claim 1, wherein the supply line is provided distally with a plurality of side perforations in order to fill and empty the balloon over its entire length.

4. The ultrasonic imaging system according to claim 1, further comprising pressure control means for controlling the pressure inside the balloon member.

5. The ultrasonic imaging system according to claim 4, wherein the pressure control means include a pilot balloon.

6. The ultrasonic imaging system according to claim 4, wherein the pressure control means include a safety valve or a pressure monitor.

7. The ultrasonic imaging system according to claim 1, further comprising positioning means for determining the position of the transmission device.

8. A method for ultrasonically scanning a patient's organ through the patient's trachea with an ultrasound endoscope device positioned in the patient's esophagus wherein the trachea is between the organ to be scanned and the ultrasound device and has fluid therein that does not efficiently transmit ultrasonic energy, thereby providing an ultrasonic gap, wherein the method comprises the steps of: positioning a transmission device, having a distensible balloon member connected to a supply line, into the patient's trachea and into the transmission path for sound waves being emitted from the endoscope; filling the distensible balloon member with a sound wave transmission fluid; positioning the ultrasound endoscope device in the atient'esophagus; and visualizing said organ by emitting sound waves through the balloon member.

9. An ultrasonic imaging system, comprising:
   an ultrasound endoscope device for scanning a patient's organs, the endoscope device being shaped and dimensioned so as to be inserted into the patient's esophagus, thus forming an intra-esophageal endoscope device; and
   a transmission device, formed by a distensible balloon member connected to a supply line to permit fluid entry in the balloon member, the balloon member and supply line being shaped and dimensioned so as to be inserted into the patient's trachea, thus forming an intra-tracheal transmission device, which is spatially separated from the endoscope device;
   wherein the balloon member is distensible to a circumferential dimension that exceeds the inner circumferential dimension of the trachea, the balloon member being arranged to fold inwardly to accommodate the excess circumferential length and to conform closely to the inside of the trachea when distended while excess material forms inwardly directed folds.

10. The imaging system according to claim 9, wherein said balloon member is made from polyurethane or a polyurethane-based synthetic material.

11. The imaging system according to claim 10, wherein the balloon member has a wall thickness between 2 and 25 microns.

12. The imaging system according to claim 10, wherein the balloon member has a wall thickness between 5 and 10 microns.

13. The imaging system according to claim 9, further including pressure control means for controlling the pressure inside said balloon member to a value of 30 mbar or less.

14. A transmission device configured for use with an ultrasound intra-esophageal endoscope device for scanning a patient's organs, wherein the transmission device is adapted to bridge a gap produced by an organ having a fluid therein that does not efficiently transmit ultrasonic energy and wherein the transmission device comprises a flexible balloon member connected to a supply line for a sound wave transmission fluid medium, the balloon member being distensible to a circumferential dimension that exceeds the inner circumferential dimension of the trachea and being arranged to fold inwardly to accommodate said excess circumferential length and to conform closely to the inside of the trachea when distended while excess material forms inwardly directed folds.

15. The transmission device according to claim 14, wherein the balloon member is made from polyurethane or a polyurethane-based synthetic material.

16. The transmission device according to claim 15, wherein the balloon member has a wall thickness between 2 and 25 microns.

17. A method for ultrasonically scanning a patient's organ with an ultrasound device positioned in the patient's esophagus between the organ to be scanned and the ultrasound device and has fluid therein that does not efficiently transmit ultrasonic energy, thereby providing an ultrasonic gap, wherein the method comprises the steps of:

positioning a transmission device for sound waves within the trachea between the organ to be scanned and the ultrasound device into the transmission path for sound waves being emitted from an endoscope, the transmission device formed by a distensible balloon member connected to a supply line to permit fluid entry in the balloon member, the balloon member distensible to a circumferential dimension that exceeds the inner circumferential dimension of the trachea; and supplying fluid to the balloon member so as to cause the balloon member to distend to conform closely to the inside of the trachea and to fold inwardly to accommodate said excess circumferential length;

positioning the ultrasound endoscope device in the patient's esophagus; and visualizing said organ by emitting sound waves through the filled balloon member.

18. The method according to claim 17, wherein the fluid is supplied at a pressure of 30 mbar or less.

* * * * *

UNITED STATES PATENT AND TRADEMARK OFFICE
CERTIFICATE OF CORRECTION

PATENT NO. : 7,780,599 B2 Page 1 of 1
APPLICATION NO. : 11/454470
DATED : August 24, 2010
INVENTOR(S) : Nierich It is certified that error appears in the above-identified patent and that said Letters Patent is hereby corrected as shown below:

Column 6, line 34, Claim 8, "atient's esophagus" should read -- patient's esophagus --

Signed and Sealed this

Thirtieth Day of November, 2010

David J. Kappos
*Director of the United States Patent and Trademark Office*